United States Patent
Goldfarb

(10) Patent No.: US 10,357,487 B2
(45) Date of Patent: Jul. 23, 2019

(54) COMBINATIONS OF ACETYLCHOLINESTERASE INHIBITORS AND MUSCARINIC AGONISTS AND METHODS OF USE THEREOF

(71) Applicant: Sidney J. Goldfarb, Princeton, NJ (US)

(72) Inventor: Sidney J. Goldfarb, Princeton, NJ (US)

( * ) Notice: Subject to any disclaimer, the term of this patent is extended or adjusted under 35 U.S.C. 154(b) by 0 days.

(21) Appl. No.: 15/369,417

(22) Filed: Dec. 5, 2016

(65) Prior Publication Data
US 2017/0157100 A1  Jun. 8, 2017

Related U.S. Application Data

(60) Provisional application No. 62/262,738, filed on Dec. 3, 2015.

(51) Int. Cl.
*A61K 31/27* (2006.01)
*A61K 45/06* (2006.01)
*A61P 13/00* (2006.01)
*A61P 13/02* (2006.01)
*A61P 13/10* (2006.01)
*A61K 31/445* (2006.01)

(52) U.S. Cl.
CPC .......... *A61K 31/445* (2013.01); *A61K 31/27* (2013.01); *A61K 45/06* (2013.01); *A61P 13/00* (2018.01); *A61P 13/02* (2018.01); *A61P 13/10* (2018.01)

(58) Field of Classification Search
CPC ....... A61K 31/27; A61K 31/445; A61K 45/06
USPC .................................................. 514/1.1, 252
See application file for complete search history.

(56) References Cited

U.S. PATENT DOCUMENTS

| 7,132,547 B2 * | 11/2006 | Ishihara | A61K 31/00 548/306.4 |
| 8,361,497 B2 * | 1/2013 | Miller | B29C 39/10 424/400 |
| 9,561,218 B2 * | 2/2017 | Clarence-Smith | A61K 31/4709 |
| 2006/0183733 A1 * | 8/2006 | Wills | A61K 31/132 514/214.01 |
| 2013/0289019 A1 * | 10/2013 | Chau | A61K 31/5513 514/215 |
| 2015/0030667 A1 * | 1/2015 | Kaufman | A61K 31/713 424/450 |

FOREIGN PATENT DOCUMENTS

WO  WO-2009124755 A1 * 10/2009 .......... A61K 31/122

OTHER PUBLICATIONS

Miyazato et al., "The Other Bladder Syndrome: Underactive Bladder", 2013, Reviews in Urology, 15(1), pp. 11-22. (Year: 2013).*
Uren et al., "Definition and symptoms of underactive bladder", 2017, Investig. Clin. Urol., 58(Supp 2), pp. S61-S67. (Year: 2017).*

* cited by examiner

*Primary Examiner* — My-Chau T. Tran
(74) *Attorney, Agent, or Firm* — Fox Rothschild LLP

(57) ABSTRACT

A method of treating one or more symptoms associated with underactive bladder in a patient suffering therefrom by administering to the patient a therapeutically effective amount of an acetylcholinesterase inhibitor (AChEI) and an amount of a muscarinic receptor agonist effective to reduce the volume of post void residual in the patient obtained by treatment with the AChEI alone.

11 Claims, No Drawings

COMBINATIONS OF ACETYLCHOLINESTERASE INHIBITORS AND MUSCARINIC AGONISTS AND METHODS OF USE THEREOF

CROSS-REFERENCE TO RELATED APPLICATIONS

This application claims priority under 35 U.S.C. 119(e) to U.S. provisional application Ser. No. 62/262,738 filed on Dec. 3, 2015.

BACKGROUND

Urinary retention is the inability to completely empty the bladder. A number of different pathophysiology can cause urinary retention. These include obstructive causes such as kidney stones, tumor or enlarged prostate in men, or non-obstructive causes such as weakening muscle tone or nerve related issues. Acute urinary retention is manifested with sudden onset of pain and discomfort which can potentially be a life-threatening medical condition requiring emergency treatment. Chronic urinary retention is a persistent inability to completely empty the bladder despite having an ability to urinate which can result in elevated post-void residual (PVR) urine volumes. Patients suffering from this condition can be presented with complications such as upper tract hydronephrosis.

A subset of male patients undergoing the Trans Urethral Resection of the Prostate (TURP) suffer from chronic urinary retention after the procedure. Such patients may rely on self-catheterization or tube drainage to empty their urine. Others may suffer complications from high post-void residuals (PVRs). Drug therapy are designed to shrink the prostate by inhibiting or slowing the growth of prostate cells or relax the muscular tissue in the prostate capsule and bladder neck are commonly used for address urinary issues. However, they are known to cause significant adverse events and are in certain cases ineffective. For such reasons there is a need in the art for a method of delivering more effective treatment options to improve the clinical outcomes for the patients suffering from urinary retention.

SUMMARY OF THE INVENTION

The present invention addresses the shortcomings in the art. At least one aspect of the present invention concerns methods of treating, including prophylactically treating, of patients suffering from urinary retention or an associated symptom thereof by administering to a patient in need thereof an effective amount of an acetylcholinesterase inhibitor (AChEI) and optionally an effective amount of a second active agent. Another aspect of the present invention is directed to methods of treating patients at risk of developing urinary retention by administering an effective amount of at least one AChEI either alone or in combination with a second active agent.

In one embodiment, the AChEI include such agents as donepezil, tacrine, edrophonium, physostigamine, neostigamine, pyridostigamine, rivastgmine or any combinations thereof. In another embodiment, the second active agent may be including a muscarinic receptor agonist, an alpha receptor blocker, finasteride, a narcotic, an anesthetic or any combination thereof. Suitable alpha receptor blocker includes but are not limited to prazosin, terazosin, doxazosin, alfuzosin, and tamulosin. Suitable muscarinic receptor agonist includes but are not limited to bethanechol, acethylcholine, methacoline, carbachol, muscarine, arecoline, pilocarpine or any natural alkaloid. In a preferred embodiment, the alpha receptor blockers or the muscarinic agent or both are used at lower doses than their usual prescribed doses.

In another aspect, new combinations and compositions containing at least one AChEI and at least one second active agent are described for use to improve bladder emptying. In one embodiment, the AChEI is donepezil (Aricept®). In another embodiment, the second active agent is bethanechol. In one embodiment, donepezil is able to augment the high-dose bethanechol so that patients with high PVRs can empty their bladder much more comfortably as compared to high dose bethanechol alone.

In one embodiment, methods of treating one or more symptoms associated with underactive bladder are described in a patient suffering therefrom by administering to the patient (i) a therapeutically effective amount of an AChEI and (ii) an amount of a muscarinic receptor agonist effective, reducing the volume of PVR in the patient, and alleviating the symptoms associated with high volume PVR. In one embodiment, the AChEI is donepezil and the muscarinic receptor agonist is bethanechol.

In another embodiment, the doses of respective AchEI or the muscarinic receptor agonist is tappered off to minimum effective doses or the discontinuation of either or both active ingredients. In yet another aspect, methods of treating patients at risk of developing hydronephrosis are described. In one embodiment, the combination regimen has a duration of at least one day, 3 days, 5 days, one week, 2 weeks, 3, weeks, 4 weeks, one month, 2 months, 6 months or more.

In yet another aspect, a pharmaceutical unit form is contemplated that contains an immediate release and a delayed release component. In one embodiment, the immediate release component contains at least one AChEI selected from the group consisting of donepezil, tacrine, edrophonium, physostigamine, neostigamine, pyridostigamine, rivastgmine or any combinations thereof and the delayed release component comprise at least one muscarinic agent selected from the group consisting of bethanechol, acethylcholine, methacoline, carbachol, muscarine, arecoline, pilocarpine or any natural alkaloid.

In another aspect of the present invention, methods of treating anxiety, pain, depression associated with urinary retention or urinary comprising administering to a subject in need of such treatment an effective amount of a combination of the present invention.

DETAILED DESCRIPTION OF THE INVENTION

The invention initially will be described in general terms. The present invention generally relates to novel combinations of therapeutic agents that are effective for treating urinary retention. The preferred embodiment of the invention will then be described in detail description of the invention. Reference to the preferred embodiment does not limit the scope of the invention, which is limited only by the scope of the claims.

AChEI are commonly used to treat myasthenia gravis, glaucoma, postural tachycardia syndrome, and as an antidote to anticholinergic poisoning and Alzheimer's disease. Side effects seen at high dosages are bradycardia, hypotension, hypersecretion, excess salivation, bronchoconstriction, GI tract hypermotility, decreased intraocular pressure, sweats, collapse, and urinary frequency. Atropine is the antidote. Donepezil marketed under the trade name Aricept is a AChEI that prevents the breakdown of acetylcholine by cholinesterase and is used in the palliative treatment of Alzheimer disease. Donepezil is used to improve cognition and behavior of people with cognitive impairment disorders and Alzheimer, but does not slow the progression of or cure the disease.

Muscarinic receptor agonists for long have been used for their stimulating effects on smooth muscle. They typically increase tone, motility and causing peristalsis of the smooth muscle of interest such as in gastrointestinal or urinary tract. Bethanechol chloride, also called carbamyl-methylcholine chloride, is a commonly prescribed muscarinic receptor agonist for patients suffering from urinary incontinence. It is available in tablets and as an injection and is also used as a stimulant of the smooth muscle of the gastrointestinal tract. The recommended oral dosage of bethanechol ranges between 10-50 mg of bethanechol chloride 3-4 times daily. However, doses of 25 mg four times a day or higher are associated with significant side-effects, such as abdominal cramping, blurred vision, fatigue and an increase in urinary frequency.

In one aspect of the present invention concerns methods of treating, including prophylactically treating, of patients suffering from urinary retention or an associated symptom thereof by administering to a patient in need thereof an effective amount of an acetylcholinesterase inhibitor (AChEI) and optionally an effective amount of a second active agent. Another aspect of the present invention is directed to methods of treating patients at risk of developing urinary retention by administering an effective amount of at least one AChEI either alone or in combination with a second active agent.

The AChEI includes such agents as donepezil, tacrine, edrophonium, physostigamine, neostigamine, pyridostigamine, rivastgmine or any combinations thereof. In another embodiment, the second active agent may be including a muscarinic receptor agonist, an alpha receptor blocker, finasteride, a narcotic, an anesthetic or any combination thereof. Suitable alpha receptor blocker includes but are not limited to prazosin, terazosin, doxazosin, alfuzosin, and tamulosin. Suitable muscarinic receptor agonist includes but are not limited to bethanecol, acetylcholine, methacoline, carbachol, muscarine, arecoline, pilocarpine or any natural alkaloid. In a preferred embodiment, the alpha receptor blockers or the muscarinic agent or both are used at lower doses than their usual prescribed doses.

In one embodiment, the course of treatment ranges from at least 2 weeks to 6 months. However, in a preferred embodiment, the amount of doses are tapered of towards discontinuation of each of the AChEI and muscarinic receptor agonist. In another embodiment, the doses of respective AchEI or the muscarinic receptor agonist is tappered off to at least 10% of their effective doses or lead to discontinuation of either or both active ingredients. In yet another aspect, methods of treating patients at risk of developing hydronephrosis are described. In one embodiment, the combination regimen has a duration of at least one day, 3 days, 5 days, one week, 2 weeks, 3 weeks, 4 weeks, one month, 2 months, 6 months or more.

In one preferred embodiment, methods are described for treating urinary retention, symptoms and complications caused by urinary retention in a patient in need thereof by following the steps of identifying a patient having an obstructed bladder, an obstructed urethra, or an obstructed ureter who is suffering from a post void residual of at least 50 ml and then administering to such patient a combination of an AChEI selected from the group consisting of donepezil, tacrine, edrophonium, physostigamine, neostigamine, pyridostigamine, rivastgmine or any combinations thereof and a muscarinic receptor agonist selected from the group consisting of bethanechol, acetylcholine, methacoline, carbachol, muscarine, arecoline, pilocarpine or any natural alkaloid and combinations thereof or at least a duration of 2 weeks, 3 weeks, 4 weeks, one month, 2 months, 6 months or more. The obstruction in a patient urinary tract can be identified by any methodology known in the art.

In one aspect of the present invention, methods of treating a patient in need of improving PVRs is described by administering an effective amount of an AChEI and an effective amount of a second active agent. In one embodiment, patients may suffer from a PVR of at least 10 ml, 20, ml, 25 ml, 50 ml, 100, ml, 200 ml, 500 ml, 1000 ml, 2000 ml or more. In yet another embodiment, patients at risk of developing PVR, such as male patients that have underwent TURP, can benefit from prophylactically being treated with a combination of AChEI and a muscarinic receptor agonist pre and/ or post TURP procedure. In a preferred embodiment, the AChEI, the alpha receptor blockers or the muscarinic agent are prescribed at 10, 25, 50, 75 percent of their FDA approved doses. At least in one embodiment, elderly patients, particularly male patients or those suffering from Alzheimer or other cognitive impairment disorder may benefit from the presently described methodologies.

The invention further provides pharmaceutical formulations which include therapeutically effective amounts of the AChEI, and therapeutically effective amounts of the muscarinic receptor agonist, or pharmaceutically acceptable salts, pharmaceutically acceptable solvates, or pharmaceutically acceptable salts solvated with pharmaceutically acceptable solvents thereof, and one or more pharmaceutically acceptable carriers, diluents, or excipients. The carrier(s), diluent(s) or excipient(s) must be acceptable in the sense of being compatible with the other ingredients of the formulation, capable of pharmaceutical formulation, and not deleterious to the recipient thereof. The invention also provides a process for the preparation of a pharmaceutical formulation including admixing the AChEI or pharmaceutically acceptable salts, solvates, solvated pharmaceutically acceptable salts thereof, with one or more pharmaceutically acceptable carriers, diluents or excipients.

As used herein, the term "effective amount" means that amount of a drug or pharmaceutical agent, or that amount of a combination of drugs or pharmaceutical agents that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder, as was known in the art as of the date of the present invention. The term also includes within its scope amounts effective to enhance normal physiological function, as was known in the art as of the date of the present invention.

Pharmaceutical formulations may be presented in unit dose forms containing a predetermined amount of active ingredient per unit dose. As is known to those skilled in the art, the amount of active ingredient per dose will depend on the condition being treated, the route of administration and the age, weight and condition of the patient or the pharmaceutical formulations may be presented in unit dose forms containing a predetermined amount of active ingredient per unit dose. Preferred unit dosage formulations are those containing a daily dose or sub-dose, or an appropriate fraction thereof, of an active ingredient. Furthermore, such pharmaceutical formulations may be prepared by any of the methods well known in the pharmacy art.

In another aspect, new combinations and compositions containing at least one AChEI and at least one second active agent are described for use to improve bladder emptying. In one embodiment, the AChEI is donepezil (Aricept®). In another embodiment, the second active agent is bethanechol. In one embodiment, donepezil is able to augment the high-dose bethanechol so that patients with high PVRs can empty their bladder much more comfortably as compared to high dose bethanechol alone.

Different effective dosage forms, modes of administration and dosage amounts may be determined empirically, and making such determinations is within the skill of the art. It is understood by the physician or the clinician of ordinary skill in the art that the dosage amount will vary with the activity of the particular active agent employed, course and/or progression of the disease state, the route of administration, the rate of excretion of the AChEI or selected muscarinic agonist, the renal and hepatic function of the patient, the duration of the treatment, the identity of any other drug being administered to the subject, age, size and like factors well known in the medical arts. As used herein, the term "formulation" or "composition" is intended to encompass a product comprising the specified ingredients in the specified amounts, as well as any product which results, directly or indirectly, from combination of the specified ingredients in the specified amounts.

As such the combinations of the present invention can be administered in such oral dosage forms as tablets, capsules (each of which includes sustained release or timed release formulations), pills, powders, micronized compositions, granules, elixirs, tinctures, suspensions, syrups and emulsions. Likewise, they may be administered in intravenous (bolus or infusion), subcutaneous, intramuscular or transdermal (e.g., patch) forms. The ordinarily skilled physician, veterinarian or clinician can readily determine and prescribe the effective amount of the present combination required to prevent, counter or arrest the progress of the urinary retention associated conditions.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the respective active ingredient for the symptomatic adjustment of the dosage to the patient to be treated.

The components of the presently describe oral formulations are conventional pharmaceutical carriers known formulations for oral use wherein said components are mixed together or separated, for example in two tablets introduced in a capsule or in a two-compartment capsule or in a multilayer (di-layer) tablet wherein the two components are both in IR or in ER form or one of the two components is in IR form and the other is in ER form, according to known technologies. In one embodiment, the compositions of the present may be in immediate, sustained or extended release pharmaceutical formulations. For example, the present invention includes compositions that comprise from 0 to 50% of an immediate release component including a AChEI, a muscarinic receptor agonist or a combination thereof and up to 100% of an extended release particle which comprises the same or different type active ingredient.

Additionally, the therapeutic agent can be delivered in microparticles composed of various biocompatible, biodegradable polymers. Examples of these types of polymers include polyester, polyalkylcyanoacrylate, polyorthoester, polyanhydride, albumin, gelatin, and starch. An advantages of microparticles is that they provide controlled and sustained release of the agent thereby minimizing the required dosing frequency. Therefore, compositions of the present invention may contain plurality of microparticles both in immediate release or delayed forms.

The AChEI and the muscarinic receptor agonist may be administered by other appropriate route. Suitable routes include oral, rectal, nasal, and parenteral (including intravesical, subcutaneous, intramuscular, intravenous, transdermal, intradermal, intrathecal, and epidural). Administration can also be by means of a bladder pump or sustained release in the bladder. In yet another embodiment, the combination of the active ingredients may be delivered as a liquid, cream, solution, emollient, gel, or spray for direct intraurethral delivery.

The combination therapies according to the present invention include the administration of the AChEI and the muscarinic receptor agonist as well as optional use of another third active agents including a second AChEIs, a second muscarinic receptor agonists or an alpha receptor blocker, an opiate, a muscle relaxant, or an anesthetic. Such combination of agents may be administered together or separately and, when administered separately this may occur simultaneously or sequentially in any order, both close and remote in time. The amounts of the compounds of AChEI and the muscarinic receptor agonist and the other optional pharmaceutically active agent(s) and the relative timings of administration will be selected in order to achieve the desired combined therapeutic effect.

Pharmaceutical formulations adapted for oral administration may be presented as discrete units such as capsules or tablets; powders or granules; solutions or suspensions in aqueous or non-aqueous liquids; edible foams; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be used in granulating. The powder mixture can be run through a tablet machine, and if the result is imperfectly formed slugs, they can be broken into granules, and the granules can be lubricated and incorporated back into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like.

Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as, for example, by coating or embedding particulate material in polymers, waxes or the like.

The agents for use according to the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. Agents for use according to the present invention may also be delivered by the use of monoclonal antibodies as individual carriers to which the compound molecules are coupled.

The compounds may also be coupled with soluble polymers as targetable drug carriers. Such polymers can include, without limitation, polyvinylpyrrolidone, pyran copolymer, polyhydroxypropylmethacrylamide-phenol, poly-ydroxyethylaspart-amide-phenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. Pharmaceutical formulations adapted for rectal administration may also be presented as suppositories.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example, those suitable for oral administration may include flavoring agents.

Also contemplated in the present invention is a pharmaceutical combination including the AChEI and the muscarinic receptor agonist wherein at least one portion is present in immediate release and the other in delayed release form. A formulation according to the present invention typically contains from about 0.01 mg to about 500 mg of the active ingredient, preferably, from about 1 mg to about 100 mg of an AChEI, a muscarinic receptor agonist or a combination thereof. Intravenously, the most preferred doses will range from about 0.1 to about 10 mg/kg/minute during a constant rate infusion. Formulations of the present invention may be administered in a single daily dose, or the total daily dosage may be administered in divided doses of two, three or four times daily.

As noted herein, the AChEI and the muscarinic agent and optionally a third active agent such as an alpha receptor blocker can be used in combination in a single formulation to enhance the treatment regime or be administered as individual components in a combination regimen. In other words, each active ingredient can be administered separately at different times during the course of therapy or concurrently in divided or single combination forms to patients or regions of such patients in need of such therapy. The instant invention is therefore to be understood as embracing all such regimes of simultaneous or alternating treatment and the term "administering" is to be interpreted accordingly. It will be understood that the scope of combinations of the compounds of this invention with other agents useful to treat the targeted condition includes in principle any combination with any pharmaceutical composition useful for treating disorders related to urinary retention and high PVR. Such conditions can include stress, depression, anxiety, pain, sleep deprivation or the like.

In one embodiment, new methods of treating one or more symptoms associated with underactive bladder are described in a patient suffering therefrom by administering to the patient (i) a therapeutically effective amount of an AChEI and (ii) an amount of a muscarinic receptor agonist effective, reducing the volume of PVR in the patient obtained by treatment with the AChEI or muscurinic receptor agonist alone, and alleviating the symptoms associated with high volume PVR. In one embodiment, the AChEI is donepezil and the muscarinic receptor agonist is bethanechol. In yet another aspect, methods of treating patients at risk of developing hydronephrosis are described.

According to the present invention, among the preferred components donepezil may be present in amounts of from 5 mg to 30 mg, advantageously from 10 mg to 30 mg, preferably from 15 mg to 30 mg, per dosage unit; tacrine may be present in amount of from 10 mg to 120 mg, advantageously from 40 mg to 120 mg, preferably from 60 mg to 120 mg per dosage unit; tamsulosin may be present in amounts of from 0.1 mg to 1.5 mg per day; Silodosin may be present in amounts 1 mg to 15; and bethanechol may be administered in amounts ranging from 25 to 500 mg; rivastigmine or a pharmaceutically acceptable salt thereof, preferably the hydrogen tartrate, may be present in an amount (in rivastigmine) of from 1.5 mg to 18 mg, advantageously from 6 mg to 18 mg, preferably from 9 mg to 18 mg per dose unit.

In a prefered embodiment, the AChEI is donepezil and the muscarinic receptor agonist is bethanechol. In at least one embodiment, donepezil was given to subjects suffering from some degree of urinary retention. In another embodiment, donepezil was successfully initiated after a behanechol regimen to potentiate the bladder emptying effects of bethanechol.

In an exemplary embodiment, patients with history of PVR of 100 ml to 2500 ml failed bother standard drug treatment and the Trans Urethral Resection of the Prostate (TURP) procedure or combinations of both treatment options. Once the patients were initiated with a cocktail of alpha blockade, bethanechol and donepezil they were able to void. Even though bothanechol has a narrow the therapeutic window, escalating doses to maximize effects was easily achieved when donepezil was added to the regimen. In addition, patients not only show improvement in urodynamic testing but also other related conditions such as anxiety, depression, back pain, or sleep deprival associated with PVR.

In one embodiment, the presently described combination regimen improves the post void residual by reducing it to at least 50%, 75%, 85%, 90%, 95%, 98% as compared to the pretreatment volumes.

Examplary Embodiment

Eight patients aged ranging from 50 to 85 years old with history of PVR, presented with a PVR ranging from 100 to 2500 ml were monitored for their clinical responsiveness to a combination of the present invention. The patients opted for immediate TURP and pharmacological therapy with alpha blocker, bethanechol, and donepezil if needed.

Table I below provides additional details about the status and progress of these patients.

TABLE 1

| Patient | Age | Residual | End PVR | Full Regimen |
|---|---|---|---|---|
| RH | 84 | 2500 mL | 500 mL | Yes |
| JN | 83 | 1100 mL | 0 mL | Yes |
| HH | 80 | 1100 mL | 40 mL | Yes |
| MD | 54 | 1000 mL | 20 mL | Yes |
| PB | 75 | 800 mL | 10 mL | Yes |
| AJ | 63 | 2000 mL | 200 mL | Yes |

TABLE 1-continued

| Patient | Age | Residual | End PVR | Full Regimen |
|---|---|---|---|---|
| LF | 77 | 800 mL | 10 mL | Yes |
| JS | 63 | 2000 mL | 10 mL | Yes |
| PK | 50 | 1100 mL | 10 mL | No donepezil |
| Avgs | 72.3 | 1430 mL | 100 mL | No |

Initially, these patients were treated with tamsulosin 0.4 mg or 0.8 mg per day, but failed a voiding trial. Subsequently, silodosin 8 mg was added with no extra side effects, however, they again failed to the voiding trial. Bethanechol was then added to maximal recommended doses, according to package insert or Physician Desk Reference (PDR), which was 200 mg per day in divided doses. They again failed the voiding trial. Bethanocol was either added at 75 mg five times per day to their existing regimen or patients were switched to betahnocol alone at 75 mg five time per day. However, they still failed the voiding trial.

Subsequently donepezil was added in amounts ranging from 5 or 10 to their respective regimens. By adding donepezil, each patient was able to void and upon continuation of the regimen, all patients reported increasing frequency of voiding with showing more than 75% to 90% reduction in PVR upon completion of the trial. Table 1 provides a range of PVR pre and post combination regime of the present invention. The eight patients exhibited no side effects at 200 mg per day or 375 mg per day but still needed donepezil in order to void.

Patients were eventually tapered off of donepezil, and then bethanechol. The tapering off was also initiated for any alpha blocker if needed. Upon completion of the course of combination therapy, some patients were maintained on either one alpha blocker alone, or on no drugs at all. Due to the age of the patients, a number of the patients eventually deteriorated for other medical problems not associated with the PVR Conclusion Donepezil potentiated bethanechol to facilitate bladder emptying in eight sequentially seen patients, who otherwise would have required catheter drainage or self-catheterization for prolonged periods of time. Use of donepezil not only help the treatment of patients with underactive bladder function, but also dramatically improved their quality of life and their need for bladder catheter. While all patients in this series were males, females can also benefit from the present combination, particularly if no obstruction exists in their urinary tract.

While the invention has been described with references to specific embodiments, modifications and variations of the invention may be construed without departing from the scope of the invention, which is defined in the following claims.

What I claim is:

1. A method of treating one or more symptoms associated with underactive bladder in a patient suffering therefrom, comprising administering to said patient for at least two weeks a combination of an acetylcholinesterase inhibitor (AChEI) selected from the group consisting of donepezil, tacrine, edrophonium, physostigamine, neostigamine, pyridostigamine, rivastgmine or any combinations thereof and a muscarinic receptor agonist selected from the group consisting of bethanechol, acetylcholine, methacoline, carbachol, muscarine, arecoline, pilocarpine or any natural alkaloid and combinations thereof.

2. The method of claim 1, wherein said AChEI is donepezil and said muscarinic receptor agonist is bethanechol.

3. The method of claim 1, wherein said AChEI and said muscarinic receptor agonist is administered to said patient concurrently or sequentially.

4. A method of treating urinary retention and symptoms and complications caused by urinary retention in a patient in need thereof, comprising identifying a patient having an obstructed bladder, urethra, or ureter and suffering from a post void residual of at least 50 ml;
administering to said patient a combination of an AChEI selected from the group consisting of donepezil, tacrine, edrophonium, physostigamine, neostigamine, pyridostigamine, rivastgmine or any combinations thereof and a muscarinic receptor agonist selected from the group consisting of bethanechol, acetylcholine, methacoline, carbachol, muscarine, arecoline, pilocarpine or any natural alkaloid and combinations thereof, and wherein the a duration of the treatment is at least 2 weeks.

5. The method of claim 4, wherein the post void residual is reduced by at least 50% compared to the pretreatment.

6. The method of claim 4, wherein the post void residual is reduced by at least 75% compared to the pretreatment.

7. The method of claim 4, wherein the post void residual is reduced by at least 90% compared to the pretreatment.

8. The method of claim 4, further comprising reducing the dose of the respective AChEI or the muscarinic receptor agonist 4 weeks after the initiation of the treatment regimen.

9. The method of claim 4, wherein the patient also suffers from cognitive impairment disorder.

10. The method of claim 4, wherein the step of delivering an agent comprises the step of delivering a third active ingredient.

11. The method of claim 10, wherein the third active ingredient is an alpha receptor agonist selected from the group consisting of prazosin, terazosin, doxazosin, alfuzosin, and tamulosin, and a combination thereof.

* * * * *